(12) United States Patent
Ahn et al.

(10) Patent No.: US 9,706,972 B1
(45) Date of Patent: Jul. 18, 2017

(54) SYSTEMS AND METHODS FOR RECONSTRUCTION OF EMISSION ACTIVITY IMAGE

(71) Applicant: General Electric Company, Schenectady, NY (US)

(72) Inventors: Sangtae Ahn, Guilderland, NY (US); Lishui Cheng, Niskayuna, NY (US); Florian Wiesinger, Bavaria (DE); Dirk Bequé, Bavaria (DE); Sandeep Suryanarayana Kaushik, Karnataka (IN); Dattesh Dayanand Shanbhag, Karnataka (IN)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 15/278,652

(22) Filed: Sep. 28, 2016

(51) Int. Cl.
| | |
|---|---|
| G01T 1/164 | (2006.01) |
| A61B 6/00 | (2006.01) |
| G01T 1/29 | (2006.01) |
| G01T 1/17 | (2006.01) |
| A61B 6/03 | (2006.01) |
| A61B 6/02 | (2006.01) |
| G06T 7/00 | (2017.01) |

(Continued)

(52) U.S. Cl.
CPC ............ *A61B 6/5235* (2013.01); *A61B 6/025* (2013.01); *A61B 6/032* (2013.01); *A61B 6/037* (2013.01); *A61B 6/4085* (2013.01); *A61B 6/461* (2013.01); *A61B 6/502* (2013.01); *A61B 6/5205* (2013.01); *G01T 1/1642* (2013.01); *G01T 1/17* (2013.01); *G01T 1/2985* (2013.01); *G06T 3/40* (2013.01); *G06T 7/0012* (2013.01); *G06T 11/008* (2013.01); *G06T 2207/10081* (2013.01); *G06T 2207/30004* (2013.01)

(58) Field of Classification Search
CPC .................................... G01T 1/00; G01T 1/29
See application file for complete search history.

(56) References Cited

U.S. PATENT DOCUMENTS

| | | | | |
|---|---|---|---|---|
| 5,682,036 A | * | 10/1997 | Hines .................... | G01T 1/1611 250/252.1 |
| 5,959,300 A | * | 9/1999 | Hines .................... | G01T 1/1611 250/363.09 |

(Continued)

OTHER PUBLICATIONS

Erdogan et al.,"Statistical Image Reconstruction Methods for Simultaneous Emission/Transmission PET Scans", IEEE Nuclear Science Symposium and Medical Imaging Conference, vol. 3, Nov. 2-9, 1996, Anaheim, CA, pp. 1579-1583.

(Continued)

*Primary Examiner* — Kiho Kim
(74) *Attorney, Agent, or Firm* — Pabitra K. Chakrabarti

(57) ABSTRACT

Aspects of the invention relate to generating an emission activity image as well as an emission attenuation map using an iterative updation based on both the raw emission projection data and the raw radiography projection data, and an optimization function. The outputs include an optimized emission activity image, and at least one of an optimized emission attenuation map or an optimized radiography image. In some aspects an attenuated corrected emission activity image is obtained using the optimized emission activity image, and the optimized emission attenuation map.

20 Claims, 11 Drawing Sheets

(51) Int. Cl.
G06T 3/40 (2006.01)
G06T 11/00 (2006.01)

(56) References Cited

U.S. PATENT DOCUMENTS

| | | | |
|---|---|---|---|
| 6,310,968 B1* | 10/2001 | Hawkins | G01T 1/1615 250/363.04 |
| 6,381,349 B1* | 4/2002 | Zeng | G06T 11/005 382/128 |
| 7,465,927 B2 | 12/2008 | Panin et al. | |
| 8,611,628 B2 | 12/2013 | Hu et al. | |
| 8,913,810 B2 | 12/2014 | Panin et al. | |
| 8,989,845 B2 | 3/2015 | Brinks et al. | |
| 9,053,569 B2 | 6/2015 | Bal et al. | |
| 9,153,012 B2 | 10/2015 | Bredno et al. | |
| 9,155,514 B2 | 10/2015 | Panin et al. | |
| 2015/0003708 A1 | 1/2015 | Prevrhal et al. | |
| 2015/0065854 A1 | 3/2015 | Ahn et al. | |
| 2016/0174919 A1 | 6/2016 | Ahn et al. | |

OTHER PUBLICATIONS

Bousse et al.,"Maximum-likelihood joint image reconstruction and motion estimation with misaligned attenuation in TOF-PET/CT", Physics in Medicine and Biology, vol. 61, Issue: 3, Feb. 7, 2016, 10 Pages.

Berker et al.,"Attenuation correction in emission tomography using the emission data—A review", Medical Physics, vol. 43, Issue: 2, Feb. 2016, pp. 807-832.

\* cited by examiner

SYSTEMS AND METHODS FOR RECONSTRUCTION OF EMISSION ACTIVITY IMAGE

BACKGROUND

This disclosure relates generally to medical imaging, and more particularly to systems and methods for reconstructing an emission activity image.

Emission Tomography (ET), for example, Positron Emission Tomography (PET) imaging, Single Photon Emission Computed Tomography (SPECT) imaging, and the like, provides in-vivo functional information on metabolic and biochemical processes. In ET imaging, a solution including a radioactive tracer is injected into a subject (e.g., a human patient) to be scanned. Typically, the tracer moves towards and is taken up in one or more organs of the subject in which these biological and biochemical processes occur. Once a radioisotope of the tracer decays, it emits a positron, which travels a short distance before annihilating with an electron. The annihilation produces two high-energy photons i.e. gamma photons propagating in substantially opposite directions.

ET imaging uses a photon detector array arranged around a scanning area, usually in a ring-shaped pattern, in which the subject or at least a part of interest of the subject is arranged. When the detector array detects the two gamma photons within a short timing window, a so-called "coincidence" is recorded. A line connecting the two detectors that received the photons is called the Line Of Response (LOR). The reconstruction of an ET image is based on the premise that the decayed radioisotope is located somewhere on the LOR. Each coincidence may be recorded in a list by three entries, wherein two entries represent the two detectors and one entry represents the time of detection (also referred herein as emission projection data).

Based on the emission projection data acquired from an emission tomography scanner that uses the photon detector as described herein above, an emission activity image is reconstructed. The emission activity image represents the spatial and/or temporal distribution of radioactivity in the body and provides clinically useful information in oncology, cardiology or neurology applications.

One phenomenon that impacts the accuracy of reconstruction of emission activity image relates to attenuation of gamma photons traveling in the subject's body. For emission tomography to provide accurate quantitation, this attenuation needs to be appropriately taken into account during ET image reconstruction or data processing. Given a subject, an emission attenuation map, or simply an attenuation map, that represents a spatial map of linear attenuation coefficients for gamma photons (e.g., 511 keV photons for PET) is used for attenuation correction. The attenuation map obtained by some techniques and their limitations are described herein below.

A transmission scan using an external gamma photon source (e.g., 68Ge/68Ga source for 511 keV photons in PET) may be performed to extract information on attenuation. However, the transmission scan increases the scan time, and noise in the estimated attenuation map or attenuation correction factors is high due to low signal-to-noise ratio (SNR) transmission scan data. In addition, the emission tomography scanner needs to be capable of the transmission scan, and not every emission tomography scanner has the capability.

Alternatively, x-ray computed tomography (CT) scans, or simply CT scans, may be used for attenuation correction in emission tomography. X-ray CT scans are fast and may provide high SNR and high resolution CT images. In PET/CT (or SPECT/CT) scanners, no image registration is required between PET and CT (or between SPECT and CT) because PET and CT (or SPECT and CT) scanners are combined in a single gantry system. Conventionally, an x-ray CT image is reconstructed from CT projection data acquired from an x-ray CT scanner, or simply a CT scanner, and then the emission attenuation map for emission tomography is generated based on the reconstructed x-ray CT image. Since the x-ray photon energies (e.g., about 30-120 keV) are different from the gamma photon energy (e.g., 511 keV for PET), the x-ray CT image needs to be appropriately scaled to form the emission attenuation map. Conventionally, bi-linear or tri-linear scaling methods are used to scale the x-ray CT image in the Hounsfield unit in order to obtain the emission attenuation map. The scaling depends on the x-ray energy and the gamma photon energy, and needs to be calibrated for a CT contrast agent if any contrast agent is used.

Often, the trans axial field of view (FOV) of CT is smaller than that of emission tomography. In this case, the CT image is truncated or has truncation artifacts, and the emission attenuation map generated based on the CT image, accordingly, is truncated or has truncation artifacts. The truncation artifacts cause quantitation errors in the emission activity image. If a metal exists in the subject, metal artifacts may appear in the CT image and the metal artifacts are propagated into the emission attenuation map generated based on the CT image, resulting in quantitation errors in the emission activity image. As the CT dose is lowered or the number of CT views is reduced, artifacts may appear due to low dose or under-sampling in the CT image, and the artifacts may propagate into the attenuation map constructed based on the CT image.

Alternatively, the emission attenuation map and the emission activity image may be jointly reconstructed based on the emission projection data only. Such a method is called maximum likelihood reconstruction of attenuation and activity (MLAA), joint estimation or joint reconstruction. However, the problem of estimating both the emission attenuation map and the emission activity image from the emission projection data does not have a unique solution and the MLAA method usually suffers cross-talk artifacts. Although time-of-flight (TOF) information acquired from a TOF PET scanner alleviates the issues of non-uniqueness and cross-talk artifacts, it does not completely resolve them.

BRIEF DESCRIPTION

In one aspect, a method for generating an optimized emission activity image is shown. The method includes receiving raw emission projection data from an emission tomography scanner and raw radiography projection data from a radiography scanner for a subject. The method then includes acquiring an initialization dataset of an initial emission activity image and at least one of an initial emission attenuation map, or an initial radiography image for the subject. The method then includes applying a first model function to generate an estimated emission projection data using the initial emission activity image, the initial emission attenuation map, and one or more emission operators to map an emission activity image space into an emission projection data space. The method also includes applying a second model function to generate an estimated radiography projection data using the initial radiography image and at least one radiography operator to map a radiography image space into a radiography projection data space. The method includes providing a scaling function to map a radiography image space into an emission attenuation map space. The method then includes using an optimization function based on the first model function, the second model function, the scaling function, the raw emission projection data, and the raw radiography data to determine iteratively an optimized emission activity image.

In another aspect, an imaging system is provided that includes an emission tomography scanner to generate raw emission projection data for a subject; a radiography scanner to generate raw radiography projection data for the subject; an image reconstruction unit implemented using one or more processors, and a display unit to display an optimized emission activity image and an optimized emission attenuation map generated by the image reconstruction unit. The image reconstruction unit includes a data acquisition system communicatively coupled to the emission tomography scanner and the radiography scanner that receives the raw emission projection data and the raw radiography projection data, respectively, an initialization module to generate an initialization dataset of an initial emission activity image and at least one of an initial emission attenuation map, or an initial radiography image for the subject, a first model function to generate an estimated emission projection data using the initial emission activity image, the initial emission attenuation map and one or more emission operators to map an emission activity image space into an emission projection data space, a second model function to generate an estimated radiography projection data using the initial radiography image and at least one radiography operator to map a radiography image space into a radiography projection data space, a scaling function to map a radiography image space into an emission attenuation map space, and an optimization function based on the first model function, the second model function, the scaling function, the raw emission projection data, and the raw radiography data to determine iteratively an optimized emission activity image and an optimized emission attenuation map.

In yet another aspect, a computer program product is provided that includes a non-transitory computer readable medium encoding instructions that, in response to execution by at least one processor, cause the processor to perform operations mentioned in the method steps described herein above

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Aspects of the invention relate to generating an emission activity image as well as an emission attenuation map using an iterative updation based on both the raw emission projection data and the raw radiography projection data. The raw emission projection data and raw radiography projection data referred herein relates to data from the detectors of the ET/radiography scanner. This provides an advantage over the transmission scan methods, since radiography scans are much faster than transmission scans using external gamma photon sources. Further, since the raw radiography projection data are used for iteratively updating the emission activity image and the emission attenuation map, the image artifacts that would occur during radiography image reconstruction, for example in CT image reconstruction due to field of view (FOV) truncation, presence of metals, low x-ray dosage or under-sampling, do not propagate into the emission attenuation map. Similarly, the use of raw emission projection data reduces the effects of CT image metal artifacts on attenuation correction, since gamma photons are less attenuated by metals, compared to attenuation of x-ray photons by metals.

The emission activity image referred herein represents the spatial and/or temporal distribution of radioactivity. The emission activity image may be represented as an array of numbers, each of which represents the radioactivity in a corresponding voxel or pixel. The emission attenuation map referred herein represents the spatial map of linear attenuation coefficients for gamma photons. The emission attenuation map may be represented as an array of numbers, each of which represents the linear attenuation coefficient of a corresponding voxel or pixel for the gamma photon energy used. For example, for a PET system, the linear attenuation coefficients are for 511 keV photons.

Further the aspects of the invention described herein do not require that the radiography projection data be complete.

Figure 1:
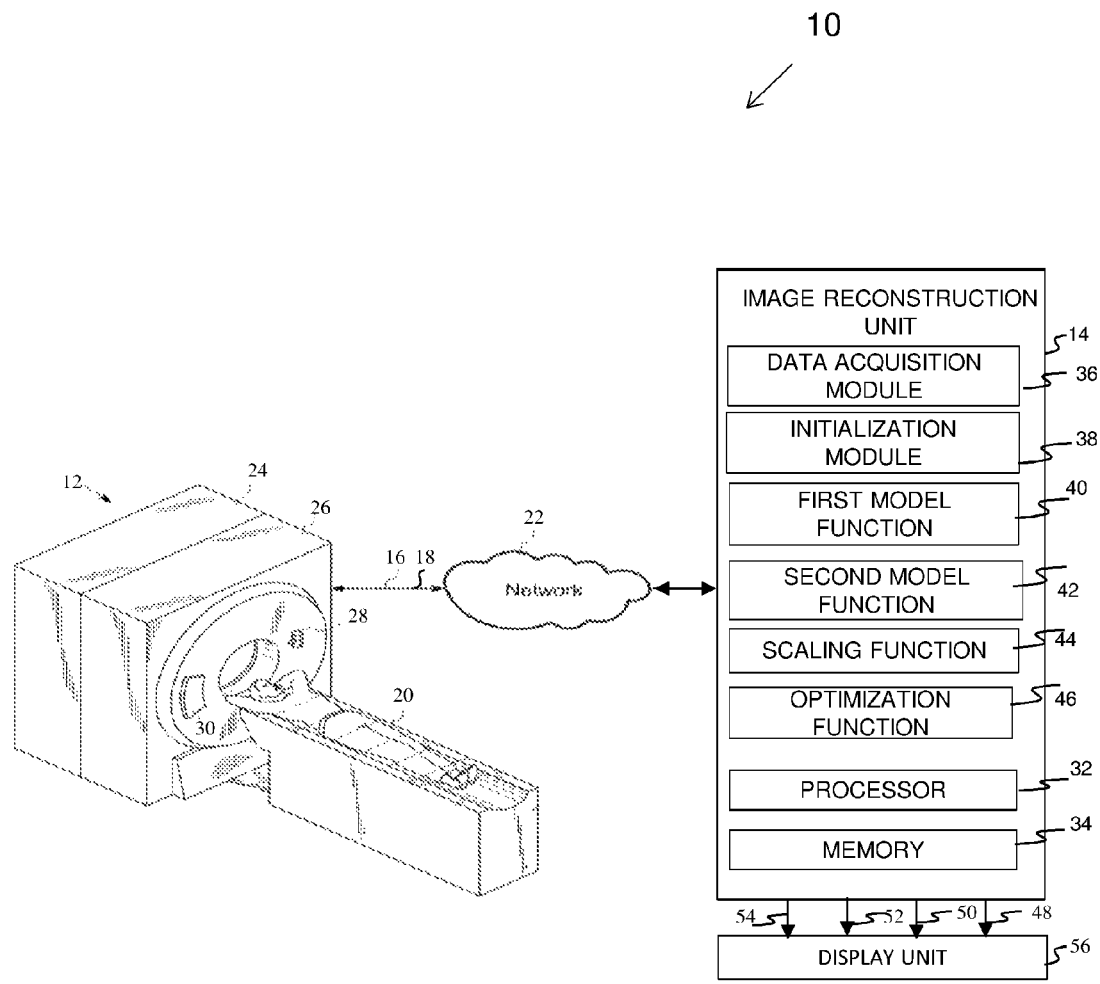
FIG. 1 is a block diagram illustrating an example of a system for Emission Tomography (ET)/Computed Tomography (CT) data acquisition of a subject.

FIG. 1 illustrates an exemplary block diagram of a system 10 for acquisition of raw emission projection data and raw radiography projection data. The system 10 includes a combined emission tomography (ET) scanner and radiography scanner 12 to acquire raw emission projection data 16 and radiography data 18 respectively for a subject 20, that are transmitted to an image reconstruction unit 14, using a network 22 and associated communication circuitry.

The ET/radiography scanner 12 may be any type of scanner configured to scan the subject 20 (e.g., a human patient, an animal, and the like) and generate the raw emission projection data 16 and the raw radiography data 18 for the subject 20. In an exemplary embodiment, the ET/radiography scanner 12 is a Positron Emission Tomography (PET) scanner/CT scanner configured to generate PET emission projection data and CT projection data of the subject 20. In another embodiment, the ET/Radiography scanner 12 is a PET/X-ray radiography scanner, and a single view is taken as a raw radiography projection data. In yet another embodiment, the ET/Radiography scanner 12 is a SPECT/CT scanner. In yet another embodiment, the ET/Radiography scanner 12 is a SPECT/X-ray radiography scanner. In some other embodiments, the radiography scanner can be implemented using a tomosynthesis scanner, where partially sampled data with limited view angles may be used a raw radiography projection data. In some other embodiments, a mammography scanner, or a cone beam computed tomography scanner may be used as a radiography scanner. Some embodiments of the invention may involve an X-ray CT scanner with irregular or arbitrary trajectories of an x-ray source or sources, and/or a detector or detectors. Still further, some embodiments may represent a case, where an axial field of view (FOV) of emission tomography is longer than that of CT for quality CT images, for example, in a helical CT scan.

The ET/radiography scanner 12 includes an ET gantry 24 and a radiography gantry 26 with respective detector components. Under operation, one or more detectors (not shown) of the ET gantry 24 detect photons emitted indirectly by a radioactive tracer in the subject 20 and generate the raw emission projection data 16. In one implementation, the ET gantry 24 generates a list mode emission projection data that represents information (e.g., time, energy and detector index) about each detected event. In another implementation the raw emission projection data is in histogram-mode format. The emission projection data may also be two-dimensional or fully three-dimensional data. The emission projection data may include time-of-flight (TOF) measurement data if the PET or PET/CT scanner has TOF capability.

The radiography gantry 26 referred herein, includes an X-ray source 28 configured to project an X-ray beam towards the subject 20. The radiography gantry 26 further comprises an X-ray detector 30 configured to receive the X-ray beam attenuated by the subject 20 and generate the raw radiography projection data 18. In the implementation using CT, the raw radiography projection data is the CT projection data acquired in axial, helical or spiral scan mode. The CT projection data may be incomplete or partially sampled projection data. In some embodiments, the CT projection data may be acquired for sparsely sampled view angles. In another embodiment, the CT projection data may be acquired for only one view angle as in x-ray radiography. That is, the CT projection data may represent x-ray radiography data. In some other embodiment, the CT projection data may represent tomosynthesis data. In another embodiment, the CT projection data may be pre-processed, for example, for beam hardening correction. Some other pre-processing including normalization and correction may also be applied to the CT projection data. For example, a logarithm operation may be applied to the CT projection data.

The image reconstruction unit 14 is communicatively coupled to the emission tomography/radiography scanner 12 through the network 22, and is implemented using a processor 32 and memory 34.

A data acquisition unit 36 of the image reconstruction unit 14 receives the raw emission projection data 16 and radiography data 18 from the ET/radiography scanner 12. It would be appreciated by those skilled in the art, that in some implementations, the data acquisition unit 36 is external to the image reconstruction unit 14. The emission projection data may be two-dimensional or fully three-dimensional data. The emission projection data may include time-of-flight (TOF) measurement data if the PET or PET/CT scanner has TOF capability.

The data acquisition unit 36 includes codes and routines configured to receive the raw emission projection data 16 and radiography data 18 from the ET/radiography scanner 12. In one embodiment, the data acquisition unit 36 includes a set of instructions executable by the processor 32 to provide the functionality for receiving the raw emission projection data 16 and radiography data 18 from the ET/radiography scanner 12. In another embodiment, the data acquisition unit 36 is stored in the memory 34 and is accessible and executable by the processor 32. In either embodiment, the data acquisition unit 36 is adapted for communication and cooperation with the processor 32 and other components of the image reconstruction unit 14.

The image reconstruction unit 14 includes an initialization module 38 for generating an initialization dataset of an initial emission activity image, and at least one of an initial emission attenuation map, or an initial radiography image for the subject. In one embodiment, the initial emission attenuation map and the initial radiography image may be separately initialized. In another embodiment, only one of the emission attenuation map and the radiography image may be initialized, and the other is initialized based on the initialized one and a scaling function described herein below. The initial emission activity image and the at least one of the initial emission attenuation map and the initial radiography image may be derived using uniform images. A uniform image represents an image whose voxel (or pixel) values are some constant (e.g., 1). The voxel (or pixel) values for the background region of the uniform image may be zero. In some embodiment, a body boundary of the subject may be extracted and used for generating the initial images. For example, the body boundary may be extracted from an emission activity image reconstructed from the emission projection data only without attenuation correction, or a radiography image reconstructed from the radiography projection data only. In another embodiment, the radiography image may be initialized using a radiography image reconstructed from the radiography projection data. The emission activity image may be initialized using an emission activity image reconstructed from the emission projection data only without attenuation correction, or with attenuation correction based on one of the initial emission attenuation map or the initial radiography image.

The initialization module 38 includes codes and routines configured to generate an initialization dataset of an initial emission activity image, and at least one of an initial emission attenuation map, or an initial radiography image for the subject. In one embodiment, the initialization module 38 includes a set of instructions executable by the processor 32 to provide the functionality for generating an initialization dataset of an initial emission activity image, and at least one of an initial emission attenuation map, or an initial radiography image for the subject. In another embodiment, the initialization module 38 is stored in the memory 34 and is accessible and executable by the processor 32. In either embodiment, the initialization module 38 is adapted for communication and cooperation with the processor 32 and other components of the image reconstruction unit 14.

The image reconstruction unit 14 further includes a first model function 40 for generating an estimated emission projection data using the initial emission activity image, the initial emission attenuation map, and one or more operators for mapping an emission activity image space into an emission projection data space.

There are two aspects of the first model function 40. In a first aspect, the first model function 40 is a deterministic model function, or a system model function, that generates the estimated emission projection data given the initial emission activity image and the initial emission attenuation map. The deterministic model function referred herein involves a forward projection that maps an emission activity image space into an emission projection data space. The deterministic model function may involve a factor to incorporate attenuation based on the initial emission attenuation map. The deterministic model function may also involve other factors to incorporate scatters, random coincidences, detector normalization, radioactive decay, scan duration, detector response models and so on. In a second aspect the first model function 40 is also a statistical noise model function for the emission projection data space. A Poisson noise model function or a Gaussian noise model function may be used for the statistical noise model function. In some embodiments, the statistical noise model function for the emission projection data space may not be explicitly chosen, and for such cases, a Gaussian noise model function may be assumed. The statistical noise model function determines a measure of goodness of fit, which summarizes the discrepancy between estimated emission projection data and the raw emission projection data. The statistical noise model is used for an optimization function 46 below.

The first model function 40 includes codes and routines configured to generate the estimated emission projection data using the initial emission activity image, the initial emission attenuation map, and the one or more operators for mapping the emission activity image space into the emission projection data space. In one embodiment, the first model function 40 includes a set of instructions executable by the processor 32 to provide the functionality for generating an estimated emission projection data using the initial emission activity image, the initial emission attenuation map, and one or more operators for mapping the emission activity image space into the emission projection data space. In another embodiment, the first model function 40 is stored in the memory 34 and is accessible and executable by the processor 32. In either embodiment, the first model function 40 is adapted for communication and cooperation with the processor 32 and other components of the image reconstruction unit 14.

A second model function 42 is provided for generating an estimated radiography projection data using the initial radiography image and at least one radiography operator for mapping a radiography image space into a radiography projection data space.

A radiography image may be represented as an array of numbers, each of which represents the linear attenuation coefficient of a corresponding pixel or voxel for the x-ray photon energy used. The radiography image may be represented in the Hounsfield unit scale. As mentioned herein above, the radiography image is mentioned by way of example, and is representative for a CT image, a tomosynthesis image, or a mammography image.

Just like the first model function mentioned herein above, the second model function also has two aspects. In the first aspect, the second model function is a deterministic model function, or a system model function, that estimates radiography projection data given an initial radiography image. The deterministic model function may involve a forward projection that maps the radiography image space into the radiography projection data space. The second aspect of the second data model function is that it includes a statistical noise model function for the radiography projection data space. A Poisson noise model function, a modified Poisson noise model function such as shifted Poisson, or a Gaussian noise model function may be used for the statistical noise model. In some embodiments, the statistical noise model function for the radiography projection data space may not be explicitly constructed, and in such cases, a Gaussian noise model may be assumed. The statistical noise model is used for an optimization function 46 below.

The second model function 42 includes codes and routines configured to generate the estimated radiography projection data using the initial radiography image and at least one radiography operator for mapping the radiography image space into the radiography projection data space. In one embodiment, the second model function 42 includes a set of instructions executable by the processor 32 to provide the functionality for an estimated radiography projection data using the initial radiography image and at least one radiography operator for mapping a radiography image space into a radiography projection data space.

In another embodiment, the second model function 42 is stored in the memory 34 and is accessible and executable by the processor 32. In either embodiment, the first model function 40 is adapted for communication and cooperation with the processor 32 and other components of the image reconstruction unit 14.

The image reconstruction unit 14 further includes a scaling function 44 for mapping a radiography image space into an emission attenuation map space. In one embodiment the scaling function alternately represents mapping of an emission attenuation map space into a radiography image space. It would be understood by those skilled in the art that the energies of the x-ray photons used in acquiring the radiography projection data and the gamma photons used in acquiring the emission projection data are different. The scaling function is used for the conversion of the linear attenuation coefficients for different photon energies. Conventionally, a bi-linear scaling model or a tri-linear scaling model is used for scaling a CT image to form the emission attenuation map. The scaling depends on the x-ray photon energy and the gamma photon energy. In addition, the scaling function may take into account a contrast agent if used for radiography imaging.

The scaling function 44 includes codes and routines configured to map the radiography image space into the emission attenuation map space. In one embodiment, the scaling function 44 includes a set of instructions executable by the processor 32 to provide the functionality for mapping the radiography image space into the emission attenuation map space. In another embodiment, the scaling function 44 is stored in the memory 34 and is accessible and executable by the processor 32. In either embodiment, the scaling function 44 is adapted for communication and cooperation with the processor 32 and other components of the image reconstruction unit 14.

An optimization function 46 is then generated based on the first model function 40, the second model function 42, the scaling function 44, the raw emission projection data 16 and the raw radiography data 18 for determining iteratively an optimized emission activity image 48. Some examples of the optimization function are described later. Several other outputs, may be further generated by the image reconstruction unit 14, and some exemplary outputs are mentioned below.

In one embodiment, the image reconstruction unit 14 further generates an optimized emission attenuation map 50 using the optimization function 46. In a further implementation of this embodiment, the image reconstruction unit 14 further generates an optimized radiography image 52 using the scaling function 44 and the optimized emission attenuation map 50. In yet another implementation, the image reconstruction unit 14 further generates an attenuation corrected emission activity image 54 using the raw emission projection data 16, and at least one of the optimized emission attenuation map 50 or the optimized radiography image 52.

In yet another embodiment, the image reconstruction unit 14 further generates the optimized radiography image 52 using the optimization function 46.

In yet another embodiment, the image reconstruction unit 14 further generates both the optimized emission attenuation map 50 and the optimized radiography image 52 using the optimization function 46.

As mentioned herein, iterative determination involves using one or more numerical optimization algorithms. Further, determining iteratively includes generating an iterative emission activity image, and at least one of an iterative emission attenuation map, or an iterative radiography image. In one implementation, the iterative emission activity image, and the at least one of the iterative emission attenuation map, or the iterative radiography image are generated in an alternate sequence. In another implementation, the iterative emission activity image, and the at least one of the iterative emission attenuation map, or the iterative radiography image are generated simultaneously.

The optimization function 46 includes codes and routines configured to determine iteratively an optimized emission activity image 48, and other outputs mentioned herein above. In one embodiment, the optimization function 46 includes a set of instructions executable by the processor 32 to determine iteratively an optimized emission activity image 48, and other outputs mentioned herein above. In another embodiment, the optimization function 46 is stored in the memory 34 and is accessible and executable by the processor 32. In either embodiment, the optimization function 46 is adapted for communication and cooperation with the processor 32 and other components of the image reconstruction unit 14.

A display unit 56 receives an output from the image reconstruction unit 14, for example, an optimized emission activity image 48, an optimized emission attenuation map 50, an optimized radiography image 52, or/and an attenuation corrected emission activity image 54, for displaying the output. In some embodiments the display unit 56 may be provided on an external communicating device or an external computing device, or may be a part of a monitoring device associated with the ET/radiography scanner 12.

The display unit 56 includes codes and routines configured to display the outputs mentioned herein above. In one embodiment, the display unit 56 includes a set of instructions executable by the processor 32 to display the outputs mentioned herein above. In another embodiment, the display unit 56 is stored in the memory 34 and is accessible and executable by the processor 32. In either embodiment, the display unit 56 is adapted for communication and cooperation with the processor 32 and other components of the image reconstruction unit 14.

Further details of functionality of the image reconstruction unit and the different modules and functions will be described in more detail in reference to the method, as an aspect of the invention herein below in relation to FIG. 2-5.

As mentioned herein above, the data communication from the ET/radiography scanner 12 to the data acquisition module 36 is done through the network 22, that may be a wired or wireless type, and may have any number of configurations such as a star configuration, token ring configuration, or other known configurations. Furthermore, the network may include a local area network (LAN), a wide area network (WAN) (e.g., the internet), and/or any other interconnected data path across which multiple devices may communicate. In one embodiment, the network may be a peer-to-peer network. The network may also be coupled to or include portions of a telecommunication network for sending data in a variety of different communication protocols. In one embodiment, the network may include Bluetooth communication networks or a cellular communications network for sending and receiving data such as via a short messaging service (SMS), a multimedia messaging service (MMS), a hypertext transfer protocol (HTTP), a direct data connection, WAP, email, or the like.

It would be understood by those skilled in the art that the different components of the image reconstruction unit 14, the data acquisition module 36, the initialization module 38, the first model function 40, the second model function 42, the scaling function 44, the optimization function 46, that are implemented through the processor 32, and the memory 34 are coupled to a communication bus (not shown) for communication with each other and for transfer of data.

The processor 32 described herein above may include at least one arithmetic logic unit, microprocessor, general purpose controller or other processor arrays to perform computations, and/or retrieve data stored on the memory 34. In one embodiment, the processor 32 may be a multiple core processor. The processor processes data signals and may include various computing architectures including a complex instruction set computer (CISC) architecture, a reduced instruction set computer (RISC) architecture, or an architecture implementing a combination of instruction sets. In one embodiment, the processing capability of the processor 32 may be limited to supporting the retrieval of data and transmission of data. In another embodiment, the processing capability of the processor 32 may also perform more complex tasks, including various types of feature extraction, modulating, encoding, multiplexing, and the like. Other type of processors, operating systems, and physical configurations are also envisioned.

In one embodiment, the memory 34 described herein above may be a non-transitory storage medium. For example, the memory may be a dynamic random access memory (DRAM) device, a static random access memory (SRAM) device, flash memory or other memory devices. The memory may also include a non-volatile memory or similar permanent storage device, and media such as a hard disk drive, a floppy disk drive, a compact disc read only memory (CD-ROM) device, a digital versatile disc read only memory (DVD-ROM) device, a digital versatile disc random access memory (DVD-RAM) device, a digital versatile disc rewritable (DVD-RW) device, a flash memory device, or other non-volatile storage devices. The memory 34 stores data that is required for the image reconstruction unit 14 to perform associated functions. In some embodiments, the memory 34 stores the different components of the image reconstruction unit 14. In some embodiments, the memory 34 stores the different outputs from the image reconstruction unit 14, as well as the raw emission projection data 16 and raw radiography data 18. Furthermore, the memory 34 stores the processed output of each individual component of the image reconstruction unit 14, i.e. the output generated by the initialization module, the output generated by the first model function, second model function, scaling function, and the output from the optimization function.

A non-limiting implementation of the different aspects of the invention described herein above is explained below:

Let $y^{PET}$ denote a vector representing PET projection data acquired in histogram mode and $y^{CT}$ denote a vector that represents CT projection data.

The deterministic (or system) model function of the first model function i.e. a PET projection data model function may be written as:

$$\bar{y}_i^{PET}(\lambda, \mu^{PET}) = \exp(-[G\mu^{PET}]_i)[P\lambda]_i + r_i \qquad \text{Equation 1}$$

where i denotes the data bin index,
$\bar{y}^{PET}$ denotes a vector representing estimated PET projection data,
$\mu^{PET}$ denotes a vector representing a PET attenuation map,
$\lambda$ denotes a vector representing a PET activity image,
G is a matrix (or operator) whose (i,j)th element represents the contribution of voxel j to the line of response (LOR) for data bin i (for example, the length of the segment of the LOR for data bin i that intersects with voxel j), P is a matrix (or operator) that maps a PET activity image space into the PET projection data space, and $r_i$ represents background contributions such as scatters and random coincidences.

Here P may model geometric forward projection, detector efficiencies, geometric calibration, scan duration, radioactive decay, dead-time, point spread function and so on except for attenuation and additive backgrounds such as scatters and random coincidences. Note that G and P may be called emission operators. Also, note that $\bar{y}_i^{PET}(\bullet, \mu^{PET})$ is an operator maps a PET (emission) activity image space into a PET (emission) projection data space.

A Poisson noise model may be used for the statistical noise model function of the PET projection data model function described herein above. In other words, the PET projection data, $y_i^{PET}$ are modeled as independent Poisson random variables whose means are $\bar{y}_i^{PET}$.

Similarly, the deterministic (or system) model function for the second model function, i.e. a CT projection data model function may be written as:

$$\bar{y}_i^{CT}(\mu^{CT})=[A\mu^{CT}]_i \qquad \text{Equation 2}$$

where $\bar{y}^{CT}$ denotes a vector representing estimated CT projection data, $\mu^{CT}$ denotes a vector representing a CT image, and A is a matrix (or operator) that maps the CT image into the CT projection data space. Here $\bar{y}_i^{CT}(\mu^{CT})$ is an operator that maps a CT image space into a CT projection data space. Note A may be called a radiography operator. The above equation applies to a post-log data case where the logarithm of the acquired CT projection data is taken and the sign is inverted. For a pre-log data case where the logarithm is not taken, the following model may be used:

$$\bar{y}_i^{CT}(\mu^{CT})=\exp(-[A\mu^{CT}]_i) \qquad \text{Equation 3}$$

where $\bar{y}_i^{CT}(\mu^{CT})$ is an operator that maps a CT image space into a CT projection data space.

A Gaussian noise model function may be used for the statistical noise model function of the CT projection data model. That is, the CT projection data $y_i^{CT}$ may be modeled as independent Gaussian random variables whose means are $\bar{y}_i^{CT}$ and whose variances are $w_i$ (this is used in equation 7 below).

The scaling function that maps the CT image to the PET attenuation map may be written as $$\mu^{PET}=S(\mu^{CT}) \qquad \text{Equation 4}$$

where S is a voxel-wise tri-linear transform, which is conventionally used for CT-based PET attenuation correction. Here $\mu^{PET}=S(\bullet)$ is an operator that maps a CT image space into a PET attenuation map space.

A cost function i.e. an objective function for the emission (PET) activity image, emission (PET) attenuation map and CT image, may be constructed as follows:

$$\Phi(\mu,\mu^{PET},\mu^{CT})=D^{PET}(y^{PET},\bar{y}^{PET}(\lambda,\mu^{PET}))+D^{CT}(y^{CT},\bar{y}^{CT}(\mu^{CT}))+R(\lambda,\mu^{PET},\mu^{CT}) \qquad \text{Equation 5}$$

where $D^{PET}$ and $D^{CT}$ are data fit functions for the PET and CT projection data, respectively and R is a regularization function. The following log-likelihood function may be used for the data fit function $D^{PET}$ for the PET projection data based on the PET projection data model i.e. the first model function, while ignoring constants:

$$D^{PET}(y,\bar{y})=\Sigma_i y_i \log \bar{y}_i - y_i \qquad \text{Equation 6}$$

For the data fit function $D^{CT}$ for the CT projection data, the following weighted least squares or, equivalently, the log-likelihood function based on the Gaussian noise model function, may be used based on the CT projection data model function:

$$D^{CT}(y^{CT},\mu^{CT})=\Sigma_i (1/w_i)(y_i^{CT}-[A\mu^{CT}]_i)^2 \qquad \text{Equation 7}$$

For the regularization function R, image roughness penalty functions that encourage spatial smoothness may be used.

A numerical optimization algorithm may be used to solve the following optimization function:

$$\text{minimize } \Phi(\lambda,\mu^{PET},\mu^{CT})=D^{PET}(y^{PET},\bar{y}^{PET}(\lambda,\mu^{PET}))+D^{CT}(y^{CT},\bar{y}^{CT}(\mu^{CT}))+R(\lambda,\mu^{PET},\mu^{CT}) \qquad \text{Equation 8}$$

$$\text{subject to } \mu^{PET}=S(\mu^{CT}),\lambda_i \geq 0, \mu_i^{CT} \geq 0, \mu_i^{PET} \geq 0.$$

Here $\mu^{PET}=S(\mu^{CT})$ is a constraint from the scaling function, and $\lambda_i \geq 0$, $\mu_i^{CT} \geq 0$, and $\mu_i^{PET} \geq 0$ are non-negativity constraints. Alternatively, the optimization function may be written as $$\text{minimize } \Psi(\lambda,\mu^{PET})=D^{PET}(y^{PET},\bar{y}^{PET}(\lambda,\mu^{PET}))+D^{CT}(y^{CT},\bar{y}^{CT}(S^{-1}(\mu^{PET})))+R'(\lambda,\mu^{PET}) \qquad \text{Equation 9}$$

$$\text{subject to } \lambda_i \geq 0, \mu_i^{PET} \geq 0 \qquad \text{Equation 10}$$

Here $\lambda_i \geq 0$ and $\mu_i^{PET} \geq 0$ are non-negativity constraints. Note $\bar{y}^{PET}$ may include scatter estimates $r_i$ as described in Equation 1.

For example, a gradient method may be used to solve the minimization problem above:

Initialize PET activity image: $\lambda^{(0)}$=uniform image

Initialize PET attenuation map: $\mu^{PET,(0)}$=uniform image

For i=1: $N_{iter}$ where $N_{iter}$ is a pre-determined iteration number

Update the PET activity image:

$$\lambda^{(i)} = \lambda^{(i-1)} - \alpha^{(i)} \frac{\partial \Psi}{\partial \lambda}(\lambda^{(i-1)}, \mu^{PET,(i-1)})$$

where $\alpha_i$ is a step size and $$\frac{\partial \Psi}{\partial \lambda}$$

is the gradient of the cost function $\Psi$ with respect to the PET activity image $\lambda$ (note $$\frac{\partial \Psi}{\partial \lambda}$$

is a function of the PET projection data $y^{PET}$ and the CT projection data $y^{CT}$)

Enforce the non-negativity constraint by setting $\lambda_j^{(i)}$=0 if $\lambda_j^{(i)}<0$, for all j Update the PET attenuation map: $\mu^{PET,(i)}=\mu^{PET,(i-1)}-$ $$\beta^{(i)} \frac{\partial \Psi}{\partial \mu^{PET}}(\lambda^{(i-1)},$$

$\mu^{PET,(i-1)}$) where $\beta_i$ is a step size and $$\frac{\partial \Psi}{\partial \mu^{PET}}$$

is the gradient of the cost function $\Psi$ with respect to the PET attenuation map $\mu^{PET}$ (note $$\frac{\partial \Psi}{\partial \mu^{PET}}$$

is a function of the PET projection data $y^{PET}$ and the CT projection data $y^{CT}$)

Enforce the non-negativity constraint by setting $\mu_j^{PET,(i)}=0$ if $\mu_j^{PET,(i)}<0$, for all j End the For-loop.

$\lambda^{(N_{iter})}$ and $\mu^{PET,(N_{iter})}$ are taken as an optimized PET activity image and an optimized PET attenuation map, respectively.

Figure 2:
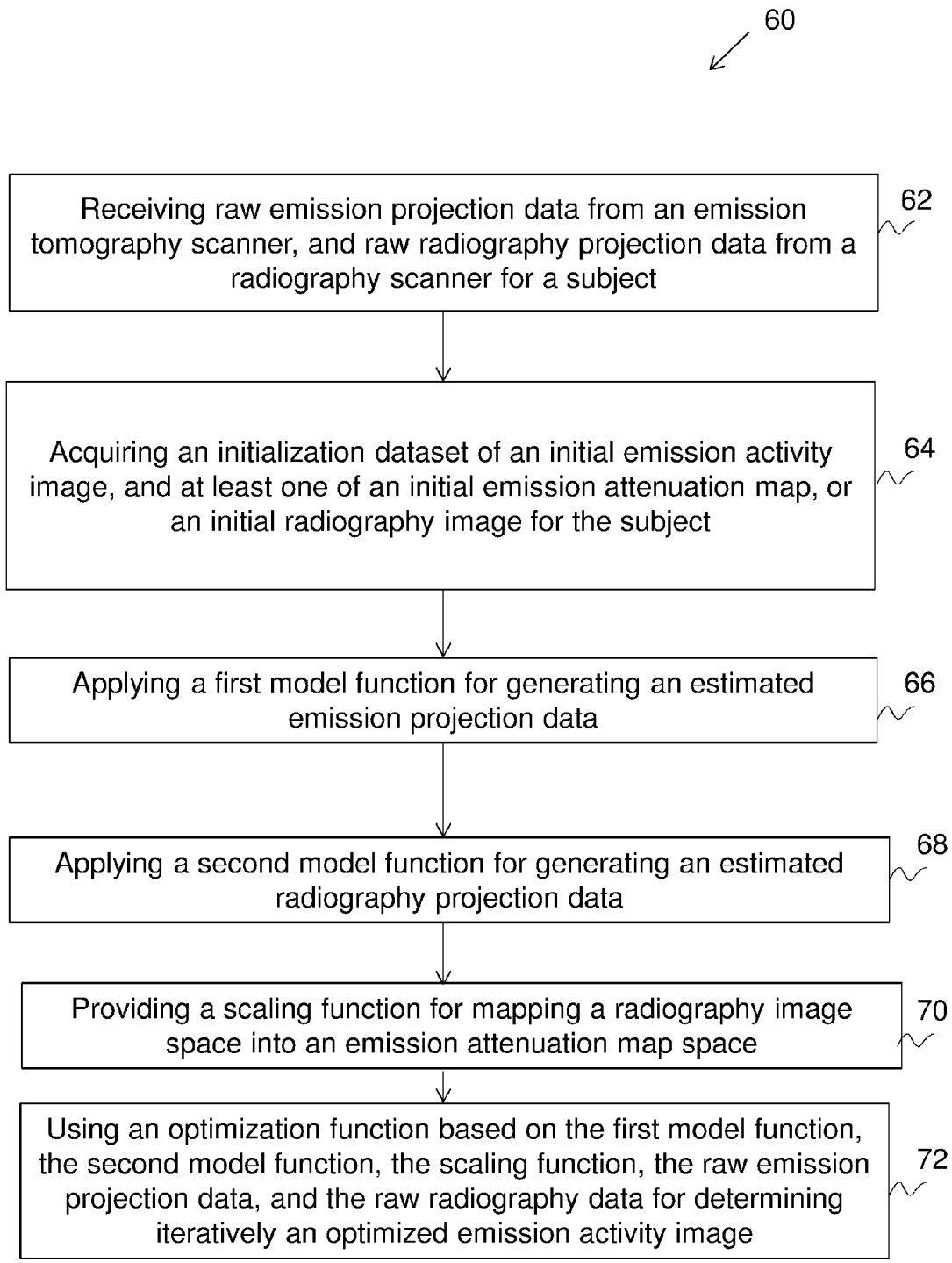
FIG. 2 is a flow chart representation of the method for generating an optimized emission activity image.

The aspects of above implementation are described as method steps for generating an optimized emission activity image in a flowchart 60 of FIG. 2. As shown in flowchart 60, the method includes a step 62 for receiving raw emission projection data from an emission tomography scanner, and raw radiography projection data from a radiography scanner for a subject as mentioned in reference to FIG. 1. The method further includes a step 64 for acquiring an initialization dataset of an initial emission activity image, and at least one of an initial emission attenuation map, or an initial radiography image for the subject.

Next, the method includes a step 66 for applying a first model function for generating an estimated emission projection data using the initial emission activity image, the initial emission attenuation map, and one or more emission operators for mapping an emission activity image space into an emission projection data space.

The method also includes as shown in step 68, applying a second model function for generating an estimated radiography projection data using the initial radiography image, and at least one radiography operator for mapping a radiography image space into a radiography projection data space.

The method further includes a step 70, for providing a scaling function for mapping a radiography image space into an emission attenuation map space.

The method then uses, as shown in step 72, an optimization function based on the first model function, the second model function, the scaling function, the raw emission projection data, and the raw radiography data for determining iteratively an optimized emission activity image. Here, determining iteratively also involves using one or more termination criteria to generate the optimized emission activity image.

In one example as described in reference to equation 5, the optimization function involves a first data fit function for the raw emission projection data based on the first model function. The optimization function also involves a second data fit function for the raw radiography projection data based on the second model function. The data fit function in one example is a sum of squared residuals, and in another example is a likelihood function based on the statistical noise model function.

The optimization function also includes a regularization function (also descried in reference to equation 5) for at least one of the emission activity space, the emission attenuation map space or the radiography image space. The one or more regularization functions may represent prior knowledge (or information) on the emission activity image, the emission attenuation map or the radiography image. For example, a roughness penalty function, a total variation function, an energy function or a Gaussian mixture based prior may be used for the regularization function.

Figure 3:
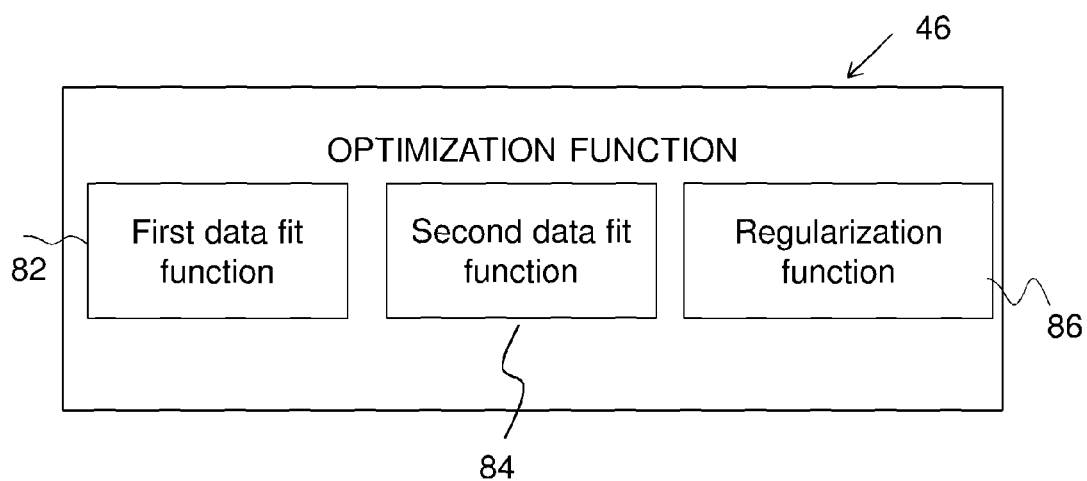
FIG. 3-7 are diagrammatic representations of an optimization function used by the system and the method aspects of the invention.

FIG. 3 is a representation for the optimization function 46 that includes the first data fit function 82, second data fit function 84 and a regularization function 86 described herein above.

Figure 4:
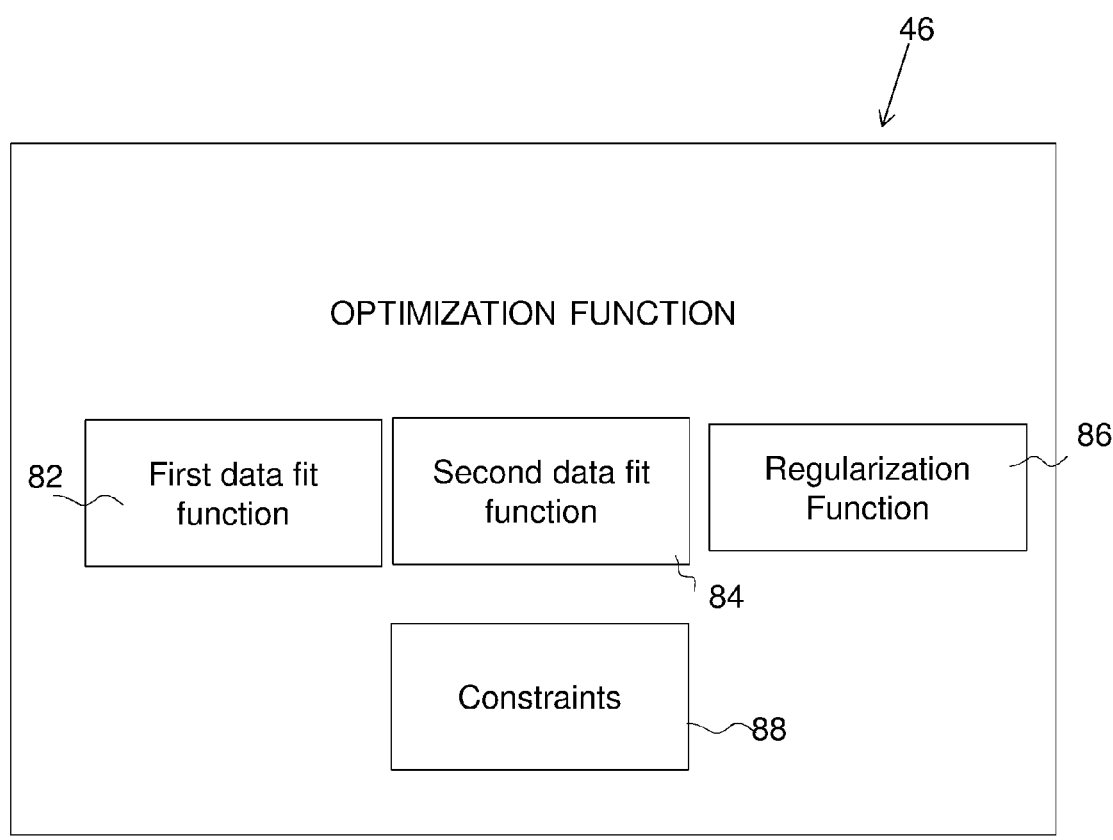
Figure 5:
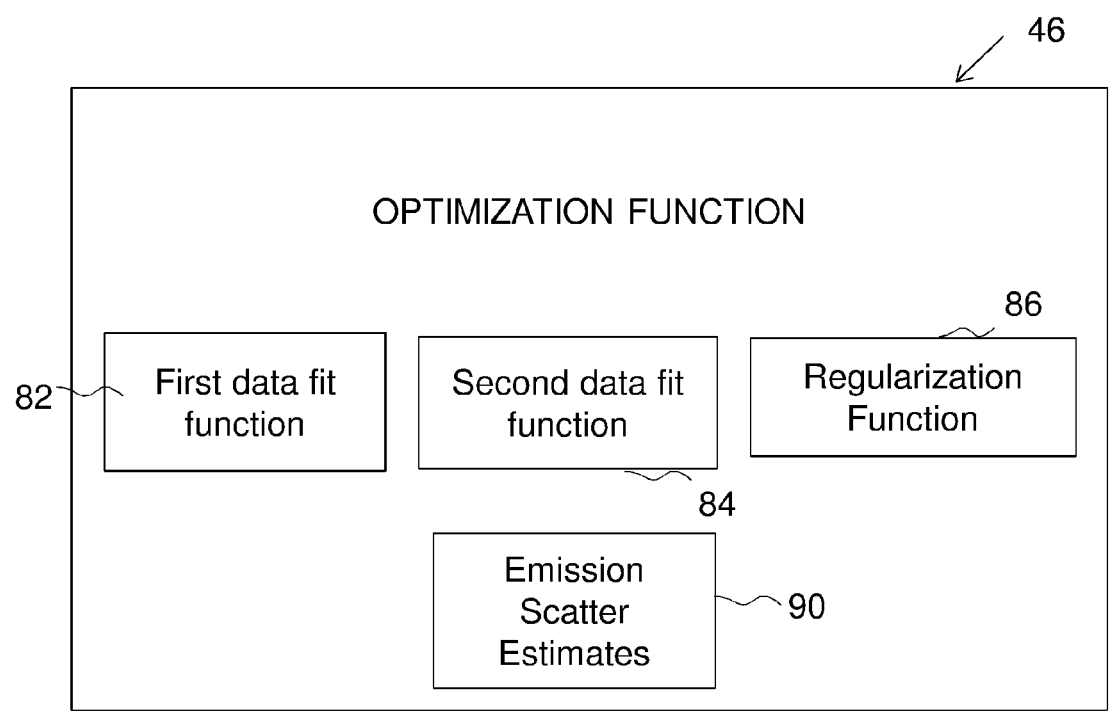

In some embodiments, as shown in FIG. 4, the optimization function 46 includes one or more constraints shown by reference numeral 88 for at least one of the emission activity space, the emission attenuation space or the radiography image space. The one or more constraints may comprise a non-negativity or positivity constraint on the emission activity image, the emission attenuation map or the radiography image In another embodiment, the optimization function 46 is further based on emission scatter estimates 90, as shown in FIG. 5. The emission scatters are estimated based on the emission projection data and the at least one of the initial emission attenuation map or the initial radiography image. The emission scatters may be estimated using a model based scatter estimation method or a Monte Carlo simulation method known to one skilled in the art. In another example, the emission scatters are estimated based on the raw emission projection data and the updated (iterative) at least one of the emission attenuation map or the radiography image.

Figure 6:
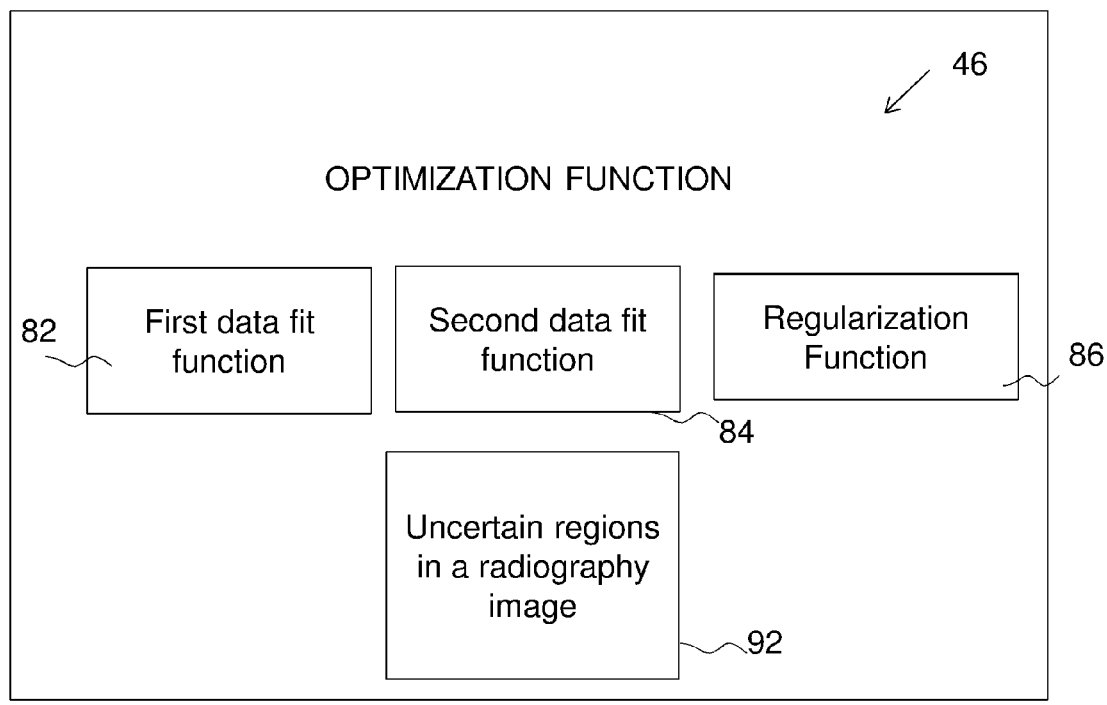

In a further embodiment, the optimization function 46 is based on identified one or more uncertain regions 92 as shown in FIG. 6 in a reconstructed radiography image generated from the raw radiography projection data and the second model function.

Figure 7:
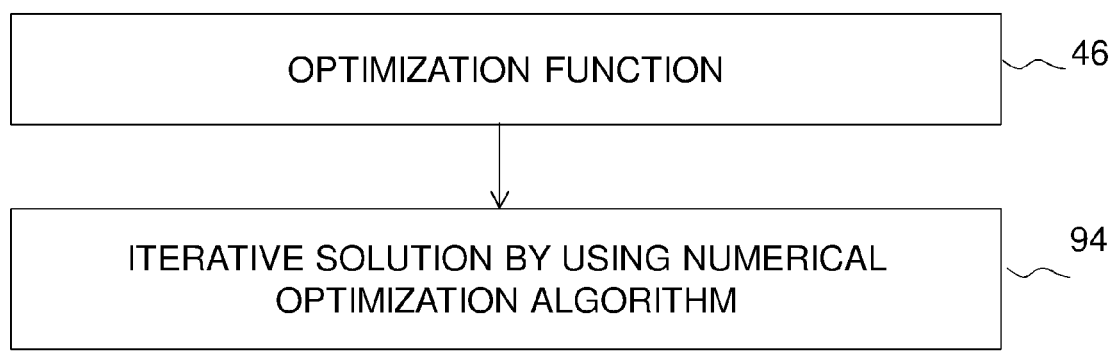

The solving of the optimization function 46 as described herein above, involves iterative solution by using one or more numerical optimization algorithms 94 as shown in FIG. 7.

Figure 8:
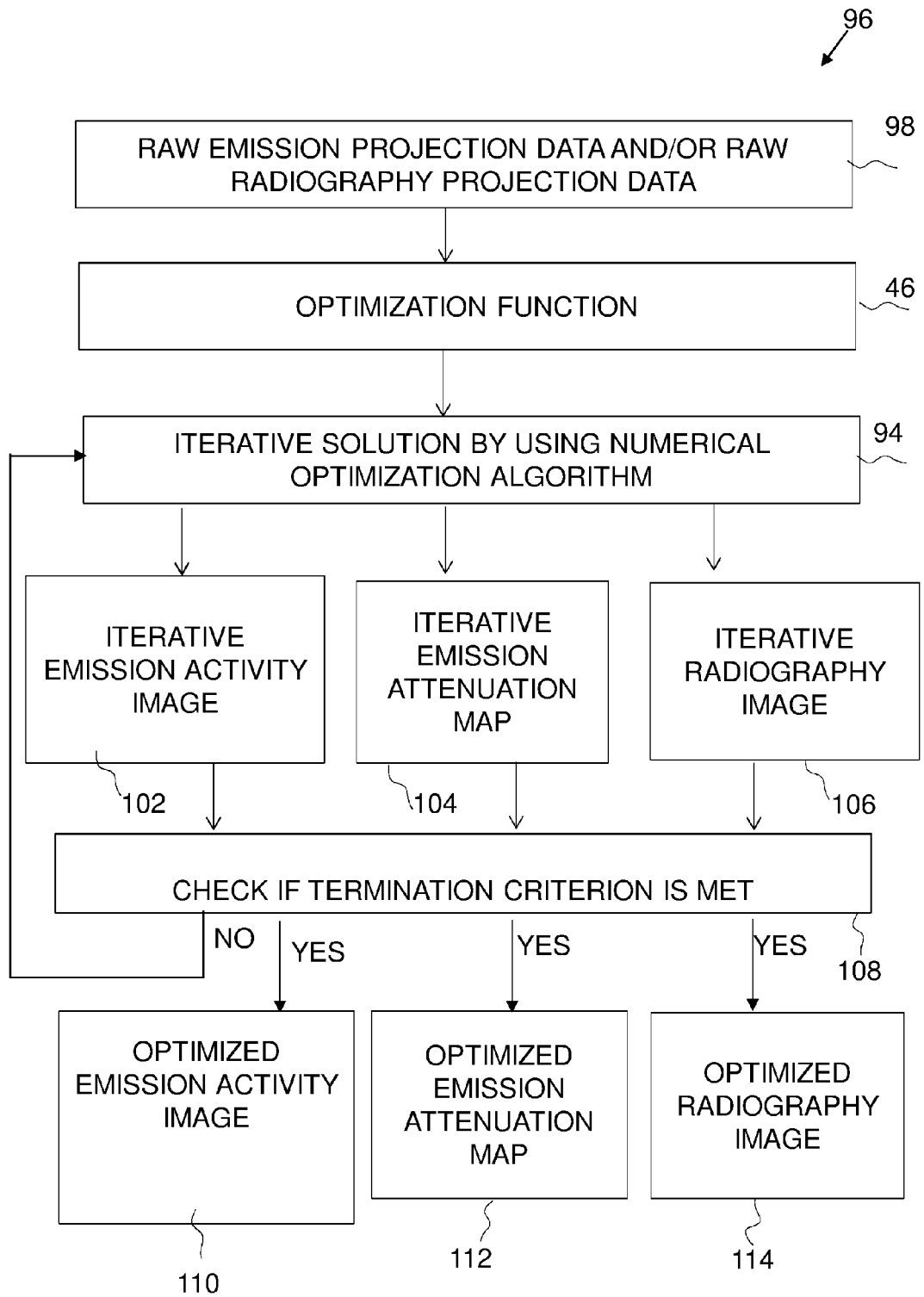
FIG. 8-11 are flow chart representations of exemplary implementations of the method described in flowchart of FIG. 2.

FIG. 8 shows an exemplary operation 96, where the raw emission projection data and/or raw radiography data is used as shown 98, with the optimization function 46, and iterative numerical algorithm solver 94. The numerical optimization algorithms update the emission activity image, shown as iterative emission activity image 102 and the at least one of the emission attenuation map, shown as iterative emission attenuation map 104 and the radiography image, shown as iterative radiography image 106, to minimize or decrease the optimization function value while satisfying the at least one constraint. For example, for the numerical optimization algorithms, expectation maximization (EM), ordered subset EM (OSEM), gradient methods, incremental gradient, stochastic gradient, conjugate gradient, coordinate descent, optimization transfer, majorize-minimize (MM), variable splitting or alternating direction method of multipliers (ADMM) may be used.

The iterative updating continues until one or more termination criteria 108 are met as shown in FIG. 8. If the one or more termination criteria are not met, the updating the emission activity image and the at least one of the emission attenuation map and the radiography image is repeated. If on the other hand, the one or more termination criteria are met, the different outputs as mentioned herein below are generated. In an example, the one or more termination criteria are based on the number of times the emission activity image and the at least one of the emission attenuation map and the radiography image are updated. In another example the termination criterion is based on a difference of the updated emission attenuation map and the previous emission attenuation map before updating. In another example, the termination criterion is based on the difference of the updated emission activity image and the previous emission activity image before updating. In yet another example, the termination criterion is based on the difference of the updated radiography image and the previous radiography image before updating. In yet another example, the termination criterion is based on a difference of the cost function values before and after updating, or the difference of the gradients of the cost function before and after updating.

It would also be appreciated by those skilled in the art that in some embodiments, the iterative emission activity image and the at least one of the iterative emission attenuation map and the iterative radiography image are updated in an alternate sequence. In a different implementation, the iterative emission activity image, and the at least one of the iterative emission attenuation map, or the iterative radiography image are updated simultaneously. In an alternative embodiment, one or more dual variables, or augmentation (or auxiliary) variables may be introduced for updation.

Several outputs are generated by using the raw emission projection data, the raw radiography data and the different functions mentioned herein above, and are shown as an optimized emission activity image 110, an optimized emission attenuation map 112, and/or an optimized radiography image 114 as shown in FIG. 8.

Figure 9:
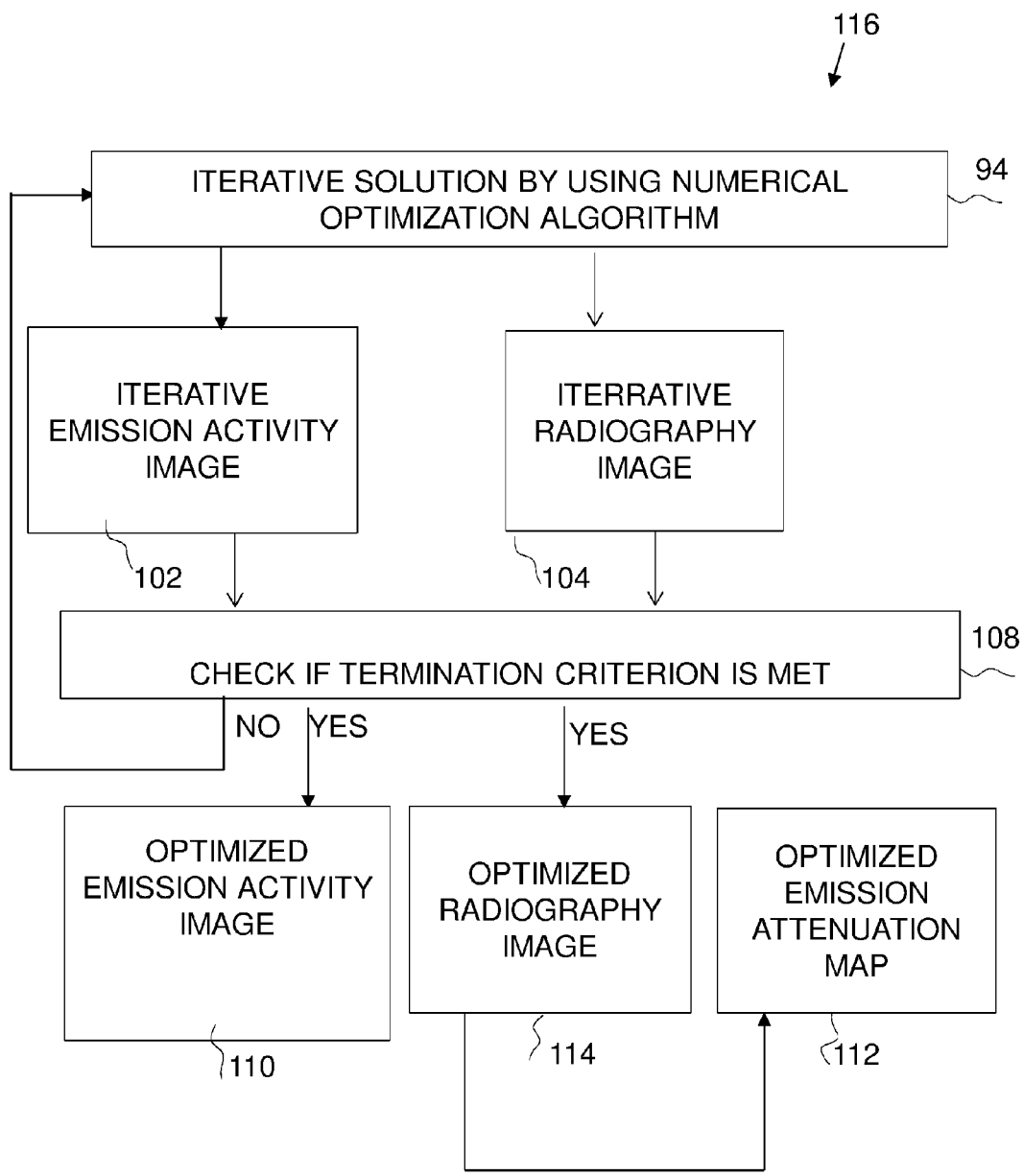
Figure 10:
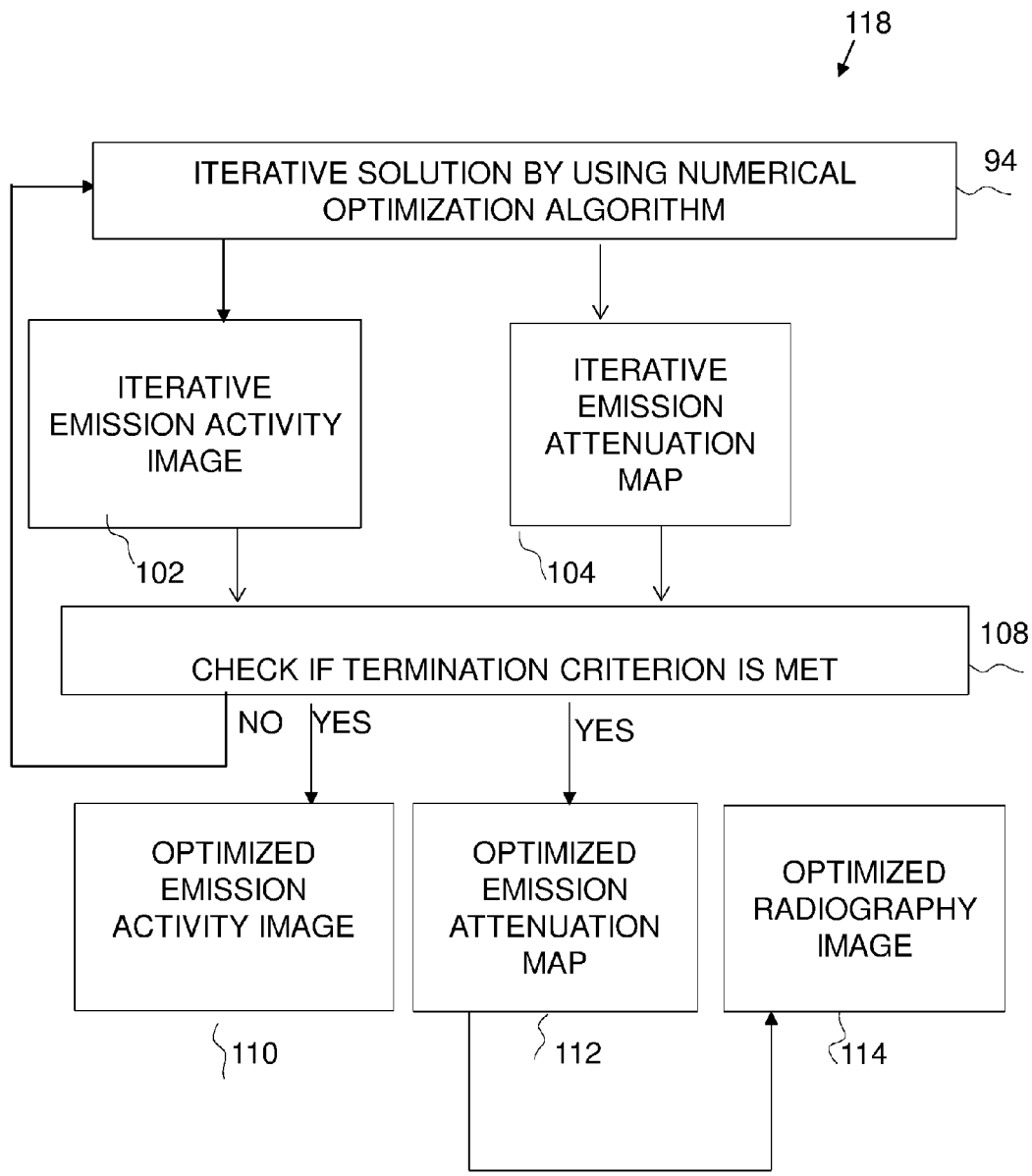

FIG. 9 and FIG. 10 illustrate two specific implementations. In FIG. 9 an optimized radiography image 114 is obtained first, and using that the optimized emission attenuation map 112 is generated. The optimized emission activity image 110 is obtained as mentioned herein above using the raw emission projection data, the raw radiography projection data, and the optimization function. In FIG. 10 an optimized emission attenuation map 112 is obtained first, and using that the optimized radiography image 114 is generated using the scaling function described herein above.

In some embodiments, for obtaining the optimized radiography image for example an optimized CT image, the CT image reconstruction is done from the raw CT projection data based on the second model function. The (initial) CT image may be reconstructed based on the raw CT projection data by using filtered-back projection (FBP), EM, OSEM, gradient methods, incremental gradient, stochastic gradient, conjugate gradient, coordinate descent, optimization transfer, majorize-minimize (MM), variable splitting or alternating direction method of multipliers (ADMM).

Next, one or more uncertain regions (or artifact regions) such as a truncated region or a metal artifact region in the reconstructed CT image are identified. For example, a truncated region may be identified based on the geometry of the CT scanner or the CT projection data. In another example, a metal artifact region may be identified by machine learning, thresholding the CT projection data followed by backprojection and image-space thresholding, or any other existing algorithm for metal artifact identification.

Next, an optimization function, i.e., a cost function and one or more constraints are determined based on the first model function, the second model function, the scaling function, and the identified one or more uncertain regions. The one or more constraints include, in an example, an equality constraint where the voxel or pixel values of the CT image are equal to those of the initial CT image for regions that do not belong to the identified one or more uncertain regions. As would be clear to one skilled in the art, the constraints may be chosen based on how the reconstructed CT image has to be used for generating an emission attenuation map. For example, a different constraint may be used, where the voxel or pixel values of an emission attenuation map are equal to those of the initial emission attenuation map for regions that do not belong to the identified one or more uncertain regions. Therefore, only the identified one or more uncertain regions in the emission attenuation map or in the reconstruction of CT image are updated, and the remaining region stays unchanged from the initial CT image.

As described herein above, the cost function and the one or more constraints may comprise a regularization function that represents a prior based on the initial CT image. Alternately, the cost function and the one or more constraints may comprise the initial emission attenuation map where the prior weights are spatially modulated based on the identified one or more uncertain regions. Low prior weights are used in the one or more uncertain regions and high prior weights are used in the remaining regions. The modulation of prior weights may be done based on techniques known in the art.

In some embodiments, the image matrix sizes of the emission attenuation map and the CT image are different, and an image transformation operation such as interpolation, down-sampling and up-sampling is performed to match the image matrix size. In a certain embodiment, image translation and/or image rotation operations are performed to match the coordinates of the emission tomography scanner and the CT scanner.

Figure 11:
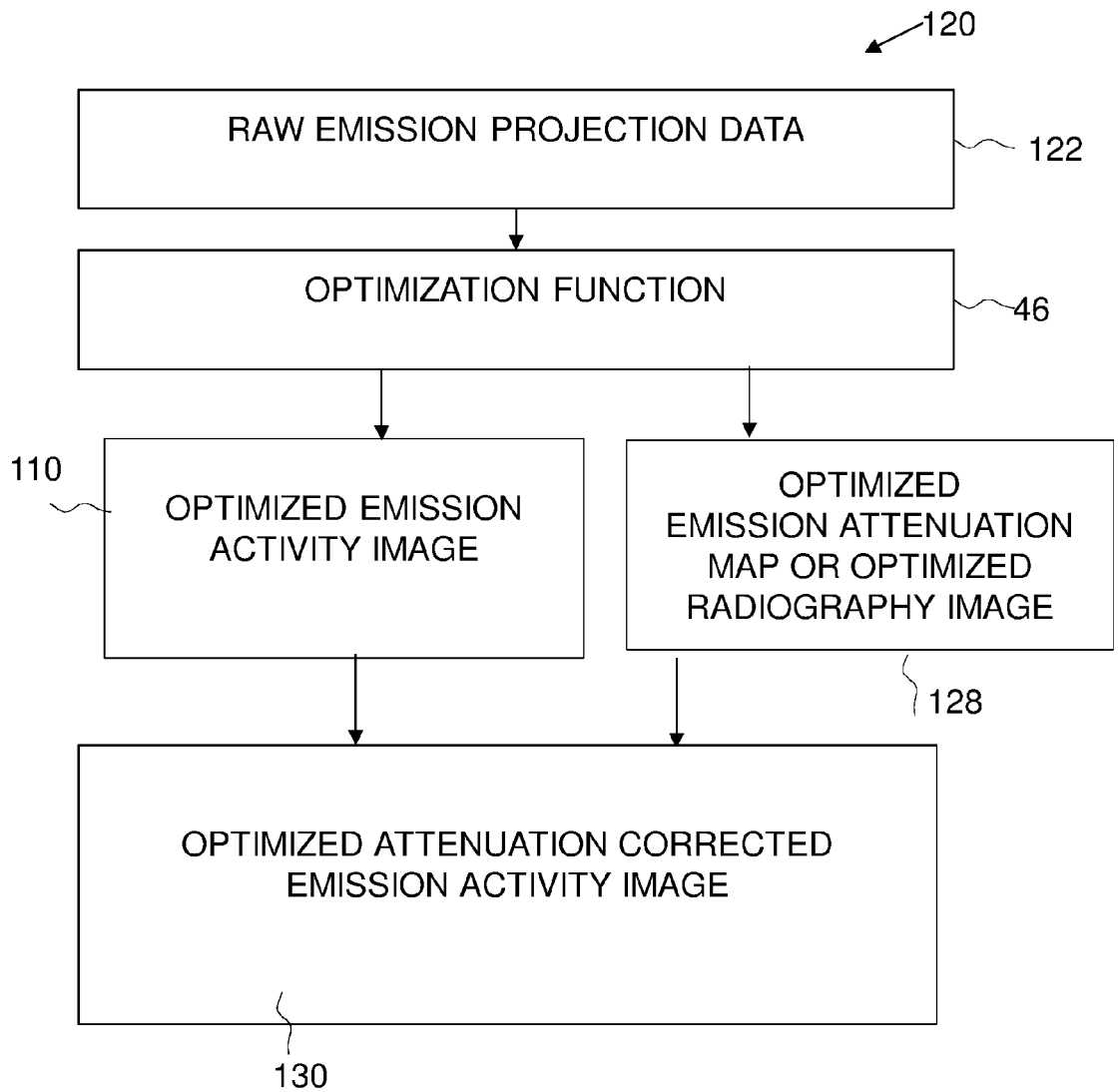

FIG. 11 shows yet another implementation 120, where an optimized attenuation corrected emission activity image 130 is generated from the optimized emission activity image 110 and/or at least one of the optimized emission attenuation map or the optimized radiography image 128, which in turn are generated using the raw emission projection data 122, and optimization function 46.

Thus the system and method provided herein allow for different flexible outputs of an ET/Radiography scan, which can be chosen on the use and need defined by a user such as a medical professional, for example a doctor.

In another aspect, a computer program product is provided that includes a non-transitory computer readable medium encoding instructions that, in response to execution by at least one processor, cause the processor to perform operations mentioned in the method steps described herein above.

The foregoing description is directed to particular embodiments of the present invention for the purpose of illustration and explanation. It will be apparent, however, to one skilled in the art that many modifications and changes to the embodiment set forth above are possible without departing from the scope and the spirit of the invention. It is intended that the following claims be interpreted to embrace all such modifications and changes.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for generating an optimized emission activity image, the method comprising:
receiving raw emission projection data from an emission tomography scanner and raw radiography projection data from a radiography scanner for a subject;

acquiring an initialization dataset of an initial emission activity image and at least one of an initial emission attenuation map, or an initial radiography image for the subject;

applying a first model function to generate an estimated emission projection data using the initial emission activity image, the initial emission attenuation map, and one or more emission operators to map an emission activity image space into an emission projection data space;

applying a second model function to generate an estimated radiography projection data using the initial radiography image and at least one radiography operator to map a radiography image space into a radiography projection data space;

providing a scaling function to map a radiography image space into an emission attenuation map space; and using an optimization function based on the first model function, the second model function, the scaling function, the raw emission projection data, and the raw radiography data to determine iteratively an optimized emission activity image.

2. The method of claim 1 further comprising generating an optimized emission attenuation map using the optimization function.

3. The method of claim 2 further comprising generating an optimized radiography image using the scaling function and the optimized emission attenuation map.

4. The method of claim 3 further comprising generating an attenuation corrected emission activity image using the raw emission projection data and at least one of the optimized emission attenuation map or the optimized radiography image.

5. The method of claim 1 further comprising determining iteratively an optimized radiography image using the optimization function.

6. The method of claim 1 further comprising determining iteratively an optimized emission attenuation map and an optimized radiography image using the optimization function.

7. The method of claim 1 wherein the optimization function comprises one or more constraints for at least one of the emission activity image space, the emission attenuation map space or the radiography image space.

8. The method of claim 1 wherein determining iteratively comprises using one or more numerical optimization algorithms.

9. The method of claim 1 wherein determining iteratively comprises generating an iterative emission activity image and at least one of an iterative emission attenuation map, or an iterative radiography image.

10. The method of claim 9 wherein the iterative emission activity image and the at least one of the iterative emission attenuation map, or the iterative radiography image are generated in an alternate sequence.

11. The method of claim 9 wherein the iterative emission activity image and the at least one of the iterative emission attenuation map, or the iterative radiography image are generated simultaneously.

12. The method of claim 1 wherein determining iteratively comprises using one or more termination criteria to generate the optimized emission activity image.

13. The method of claim 1 wherein the optimization function is further based on emission scatter estimates.

14. The method of claim 1 wherein the optimization function is further based on identified one or more uncertain regions in a reconstructed radiography image generated from the raw radiography projection data and the second model function.

15. An imaging system comprising:
an emission tomography scanner to generate raw emission projection data for a subject;
a radiography scanner to generate raw radiography projection data for the subject;
an image reconstruction unit implemented using one or more processors, comprising:
a data acquisition system communicatively coupled to the emission tomography scanner and the radiography scanner that receives the raw emission projection data and the raw radiography projection data, respectively,
an initialization module to generate an initialization dataset of an initial emission activity image and at least one of an initial emission attenuation map, or an initial radiography image for the subject,
a first model function to generate an estimated emission projection data using the initial emission activity image, the initial emission attenuation map and one or more emission operators to map an emission activity image space into an emission projection data space,
a second model function to generate an estimated radiography projection data using the initial radiography image and at least one radiography operator to map a radiography image space into a radiography projection data space,
a scaling function to map a radiography image space into an emission attenuation map space, and
an optimization function based on the first model function, the second model function, the scaling function, the raw emission projection data, and the raw radiography data to determine iteratively an optimized emission activity image and an optimized emission attenuation map; and
a display unit to display the optimized emission activity image and the optimized emission attenuation map.

16. The imaging system of claim 15 wherein the image reconstruction unit generates an optimized radiography image using the scaling function and the optimized emission attenuation map.

17. The imaging system of claim 16 wherein the image reconstruction unit further generates an attenuation corrected emission activity image using the raw emission projection data and at least one of the optimized emission attenuation map or the optimized radiography image.

18. The imaging system of claim 15 wherein the emission tomography scanner is at least one of a positron emission tomography (PET) scanner or a single photon emission computed tomography (SPECT) scanner.

19. The imaging system of claim 15 wherein the radiography scanner is at least one of an X-ray radiography scanner, a computed tomography (CT) scanner, a tomosynthesis scanner, a mammography scanner, or a cone beam computed tomography scanner.

20. A computer program product comprising a non-transitory computer readable medium encoding instructions that, in response to execution by at least one processor, cause the processor to perform operations comprising:
receiving raw emission projection data from an emission tomography scanner, and raw radiography projection data from a radiography scanner for a subject;
acquiring an initialization dataset of an initial emission activity image, and at least one of an initial emission attenuation map, or an initial radiography image for the subject;

applying a first model function to generate an estimated emission projection data using the initial emission activity image, the initial emission attenuation map, and one or more emission operators to map an emission activity image space into an emission projection data space;

applying a second model function to generate an estimated radiography projection data using the initial radiography image and at least one radiography operator to map a radiography image space into a radiography projection data space;

providing a scaling function to map a radiography image space into an emission attenuation map space; and using an optimization function based on the first model function, the second model function, the scaling function, the raw emission projection data, and the raw radiography data to determine iteratively an optimized emission activity image and an optimized emission attenuation map.

* * * * *